(12) United States Patent
Hairault et al.

(10) Patent No.: US 8,178,354 B2
(45) Date of Patent: May 15, 2012

(54) CHEMICAL SENSORS COMPRISING FLUORESCENT CONJUGATED POLYMERS AS SENSITIVE MATERIALS, AND THEIR USE IN THE DETECTION OR ASSAYING OF NITRO COMPOUNDS

(75) Inventors: Lionel Hairault, La Croix en Touraine (FR); Eric Pasquinet, Saint-Avertin (FR); Pierre Montmeat, La Riche (FR); Joël Moreau, Montpellier (FX); Jean-Pierre Lere-Porte, Montpellier (FR); Salem Wakim, Quebec (CA); Françoise Serein-Spirau, Montpellier (FR)

(73) Assignee: Commissariat a l'Energie Atomique, Paris (FR)

( * ) Notice: Subject to any disclaimer, the term of this patent is extended or adjusted under 35 U.S.C. 154(b) by 579 days.

(21) Appl. No.: 11/547,598

(22) PCT Filed: Apr. 8, 2005

(86) PCT No.: PCT/FR2005/050222
§ 371 (c)(1), (2), (4) Date: Oct. 5, 2006

(87) PCT Pub. No.: WO2005/103653
PCT Pub. Date: Nov. 3, 2005

(65) Prior Publication Data
US 2008/0044910 A1   Feb. 21, 2008

(30) Foreign Application Priority Data
Apr. 9, 2004  (FR) ..................... 04 50719

(51) Int. Cl.
*G01N 33/00* (2006.01)
(52) U.S. Cl. .................. 436/106; 436/164; 436/172
(58) Field of Classification Search ................ 436/106, 436/527
See application file for complete search history.

(56) References Cited

FOREIGN PATENT DOCUMENTS
EP   0 794 428   9/1997
EP   1 281 744   2/2003

OTHER PUBLICATIONS

Rose-Pehrrson et al. "Detection of hazardous vapors including mixtures using pattern recognition analysis of responses from surface acoustic wave devices" Anal. Chem. 1988 60(24) 2801-2811.*
Swager et al. Fluorescence Studies of Poly(p-phenyleneethynylene)s: The Effect of Anthracene Substitution. J. Phys. Chem. 1995, vol. 99, pp. 4886-4893.*
Yang et al. "Porous Shape Persistent Fluorescent Polymer Films: An Approach to TNT Sensory Materials" J. Am. Chem. Soc. 1998, vol. 120, pp. 5321-5322.*

(Continued)

*Primary Examiner* — Yelena G Gakh
*Assistant Examiner* — David Weisz
(74) *Attorney, Agent, or Firm* — Brinks Hofer Gilson & Lione (57) ABSTRACT

The invention relates to chemical sensors comprising fluorescent conjugated polymers as sensitive materials and to their use in detecting or assaying nitro compounds, in particular nitroaromatic compounds. Fields of application: detection of explosives, monitoring and observation of atmospheric pollution and of the quality of relatively confined surroundings, watching over industrial sites.

21 Claims, 3 Drawing Sheets

OTHER PUBLICATIONS

Huang, Hong-Mei, et al., "Optical membrane for o-nitroaniline based on fluorescence energy transfer between a small molecule and a conjugated polymer", Analytica Chimica Acta, 2003, pp. 109-117, vol. 481, Search Report.

Lére-Porte, Jean-Pierre, et al., "A chiral polymner with alternating conjugated segments and (1R,2R)-1,2-diaminocyclohexane as a unit with $C_2$ symmetry", Tetrahedron Letters, 2001, pp. 3073-3076, vol. 42, Search Report.

Lére-Porte, Jean-Pierre, et al., "New chiral π-conjugated polymers based on a (1R,2R)-diiminocyclohexane chiral unit with weak interchain π stacking", Chem, Commun, 2002, pp. 3020-3021, Search Report.

Miao, Yi-Jun, et al., "Fluorescence Sensory Polymers Containing Rigid Non-planar Aromatic Scaffolds", Papers presented at the meeting—American Chemical Society, Division of Polymer Chemistry, Aug. 1998, pp. 1081-1082, vol. 39, Search Report.

Tanese, M.C. et al., "Poly(phenyleneethynylene) polymers bearing glucose substituents as promising active layers in enantioselective chemiresistors", Sensors and Actuators, 2004, pp. 17-21, vol. 100, No. 1-2, Search Report.

Yang, Jye-Shane, et al., "Fluorescent Porous Polymer Films as TNT Chemosensors: Electronic and Structural Effects", J. Am. Chem, Soc., 1998, pp. 11864-11873, vol. 120., No. 46, Search Report.

* cited by examiner

CHEMICAL SENSORS COMPRISING FLUORESCENT CONJUGATED POLYMERS AS SENSITIVE MATERIALS, AND THEIR USE IN THE DETECTION OR ASSAYING OF NITRO COMPOUNDS

TECHNICAL FIELD

The present invention relates to chemical sensors comprising fluorescent conjugated polymers as sensitive materials and to their use in detecting or assaying nitro compounds, in particular nitroaromatic compounds, such as nitrobenzene (NB), dinitrobenzene (DNB), trinitrobenzene (TNB), nitrotoluene (NT), dinitrotoluene (DNT), 2,4,6-trinitrotoluene (TNT) and analogous products.

Such sensors are of use in the detection of explosives, whether for the purpose of ensuring the safety of public places, such as airports, of monitoring the lawfulness of goods circulating in a region, or combating terrorism, of carrying out disarmament operations, of locating antipersonnel mines or of decontaminating industrial or military sites. They are also of use in the protection of the environment, in particular in the monitoring and observation of atmospheric pollution and of the quality of relatively confined surroundings, and also in watching over, for security purposes, industrial sites where nitro compounds are manufactured, stored and/or handled.

PRIOR ART

The detection of explosives is a problem of crucial importance, in particular as regards civil defence.

Currently, several methods are used to detect vapours of nitro compounds which are constituents of explosives, such as the use of "sniffer" dogs, trained for this purpose, the laboratory analysis, for example by chromatography coupled to a mass spectrometer or to an electron capture detector, or samples taken on site, or infrared detection.

These methods generally prove to be highly sensitive, which is essential as regards detection of explosives, due to the very low concentration of vapours of nitro compounds prevailing in the vicinity of an explosive. However, they are not entirely satisfactory.

Thus, the use of "sniffer" dogs exhibits the disadvantage of requiring lengthy training of the dogs and of their handlers and being unsuitable for prolonged operations as the attention span of dogs is limited.

As regards the other methods, the bulkiness of the equipment which they use, their energy consumption and their operating costs conflicts with the development of detection systems which are readily transportable and autonomous and, consequently, capable of being used on any type of site.

For some years, the development of sensors capable of detecting chemical entities in real time has been advancing rapidly. The operation of these sensors is based on the use of a film of a sensitive material, that is to say of a material having at least one physical property which is modified on contact with the molecules which are being looked for, which coats a system capable of measuring in real time any variation in this physical property and of thus demonstrating the presence of the gas molecules which are being looked for.

There are many advantages to chemical sensors in comparison with the abovementioned methods: instant results, possibility of miniaturization and thus of portability, handleability and strong autonomy, low manufacturing and operating costs, and the like.

However, it is obvious that their performances are extremely variable, depending on the nature of the sensitive material used.

Various families of compounds have been provided for acting as sensitive materials in sensors for the detection of nitro compounds and in particular nitroaromatic compounds, including polysiloxanes, polyethylene glycols, amines, phthalocyanines, cyclodextrins, adsorbents, such as charcoal, and fluorescent compounds.

As regards the latter, the studies carried out to date have essentially come within two different lines of research, namely, on the one hand, the development of sensors based on nanostructured porous silicon (M. J. Sailor et al., *SPIE Proceedings*, The International Society of Optical Engineering, 3713, 1999, 54-65 [1]) or on silica in combination with an organic dye (K. J. Albert and D. R. Walt, *Anal. Chem.*, 72, 2000, 1947 [2]) and, on the other hand, the preparation of sensors using highly conjugated organic molecules.

It is known in particular that π-conjugated polymers generally exhibit high-sensitivity with regard to nitro compounds and in particular nitroaromatic compounds.

However, in order to be able to act as sensitive materials in chemical sensors, it is advisable for these π-conjugated polymers also to exhibit excellent properties of permeability, of chemical affinity and of selectivity with regard to nitro compounds, and also a high fluorescence yield. In addition, it is advisable for these properties to be stable over time, so as to confer a satisfactory lifetime on the sensors, that is to say, in practice, of several weeks, indeed even of several months.

The present invention is targeted precisely at providing a chemical sensor which comprises, as sensitive materials, fluorescent π-conjugated polymers which meet all these criteria.

ACCOUNT OF THE INVENTION

A first subject-matter of the present invention is thus a chemical sensor which comprises, as sensitive material, at least one polymer comprising at least one repeat unit corresponding to the general formula (I) below:

in which:

$A^1$, $A^2$ and $A^3$ represent, independently of one another, a substituted or unsubstituted phenyl or thienyl group; and B represents a substituted or unsubstituted chiral group of C2 symmetry or else a group corresponding to one of the formulae (a), (b) and (c) below:

where:

X represents a saturated or unsaturated, linear, branched or cyclic, hydrocarbon group comprising from 1 to 100 carbon atoms, which hydrocarbon group can comprise one or more heteroatoms and/or one or more chemical functional groups comprising at least one heteroatom, and can be a substituted or unsubstituted aromatic or heteroaromatic group or can comprise one or more substituted or unsubstituted aromatic or heteroaromatic groups;

$R^1$ and $R^2$ represent, independently of one another:
- a hydrogen or halogen atom;
- a saturated or unsaturated, linear, branched or cyclic, hydrocarbon group comprising from 1 to 100 carbon atoms, which hydrocarbon group can comprise one or more heteroatoms and/or one or more chemical functional groups comprising at least one heteroatom, and can be a substituted or unsubstituted aromatic or heteroaromatic group or can comprise one or more substituted or unsubstituted aromatic or heteroaromatic groups; or still
- a chemical functional group comprising at least one heteroatom.

In that which precedes and that which follows, the term "heteroatom" is understood as meaning any atom other than carbon or hydrogen, such as, for example, an oxygen, sulphur, nitrogen, fluorine, chlorine, phosphorus, boron or silicon atom, oxygen, sulphur and nitrogen atoms being preferred.

The term "chemical functional group comprising at least one heteroatom" is understood as meaning any chemical functional group comprising one or more atoms other than carbon or hydrogen and in particular a chemical functional group comprising one or more oxygen, sulphur, nitrogen and/or halogen atoms. This chemical functional group can in particular be chosen from the —COOH, —COOR$^3$, —CHO, —CO—, —OH, —OR$^3$, —SH, —SR, —SO$_2$R$^3$, —NH$_2$, —NHR$^3$, —NR$^3$R$^4$, —CONH$_2$, —CONHR$^3$, —CONR$^3$R$^4$, —C(Hal)$_3$, —OC(Hal)$_3$, —C(O)Hal, —CN, —COOCHO, —COOCOR$^3$ and phenol functional groups, in which:
- $R^3$ represents a saturated or unsaturated, linear, branched or cyclic, hydrocarbon group comprising from 1 to 100 carbon atoms or, in the case where said chemical functional group forms a bridge within a C$_2$ to C$_{100}$ hydrocarbon group, a covalent bond;
- $R^4$ represents a saturated or unsaturated, linear, branched or cyclic, hydrocarbon group comprising from 1 to 100 carbon atoms, which group can be identical to or different from the hydrocarbon group represented by $R^3$; while
- Hal represents a halogen atom, for example a fluorine, chlorine or bromine atom.

Moreover, the term "aromatic group" is understood as meaning any, mono- or polycyclic group which satisfies Hückel's rule, that is to say which exhibits a number of delocalized π electrons equal to (4n+2), and the term "heteroaromatic group" is understood as meaning any mono- or polycyclic group as just defined but comprising one or more heteroatoms in the ring or at least one of the rings forming it. Mention may be made, as examples of aromatic groups capable of being used, of the cyclopentadienyl, phenyl, benzyl, biphenyl, phenylacetylenyl, pyrenyl or anthracenyl groups, while mention may be made, as examples of heteroaromatic groups, of the furanyl, pyrrolyl, thienyl, oxazolyl, pyrazolyl, thiazolyl, imidazolyl, triazolyl, pyridinyl, pyranyl, quinolinyl, pyrazinyl and pyrimidinyl groups. In accordance with the invention, this aromatic or heteroaromatic group can be substituted, in particular by one or more chemical functional groups comprising at least one heteroatom, such as those mentioned above.

According to a first preferred arrangement of the invention, in the general formula (I), $A^1$, $A^2$ and $A^3$ are each a phenyl group, in which case the repeat unit of general formula (I) preferably corresponds to the specific formula (I-A) below:

in which:
$R^5$, $R^6$, $R^7$, $R^8$, $R^9$, $R^{10}$, $R^{11}$, $R^{12}$, $R^{13}$, $R^{14}$, $R^{15}$ and $R^{16}$ represent, independently of one another:
- a hydrogen or halogen atom;
- a saturated or unsaturated, linear, branched or cyclic, hydrocarbon group comprising from 1 to 100 carbon atoms, which hydrocarbon group can comprise one or more heteroatoms and/or one or more chemical functional groups comprising at least one heteroatom, and can be a substituted or unsubstituted aromatic or heteroaromatic group or can comprise one or more substituted or unsubstituted aromatic or heteroaromatic groups; or
- a chemical functional group comprising at least one heteroatom; and
- B has the same meaning as above.

According to another preferred arrangement of the invention, in the general formula (I), $A^1$ and $A^2$ are each a thienyl group, while $A^3$ is a phenyl group, in which case the repeat unit of general formula (I) preferably corresponds to the specific formula (I-B) below:

in which:
$R^5$, $R^6$, $R^9$, $R^{10}$, $R^{13}$, $R^{14}$, $R^{15}$ and $R^{16}$ represent, independently of one another:
- a hydrogen or halogen atom;
- a saturated or unsaturated, linear, branched or cyclic, hydrocarbon group comprising from 1 to 100 carbon atoms, which hydrocarbon group can comprise one or more heteroatoms and/or one or more chemical functional groups comprising at least one heteroatom, and can be a substituted or unsubstituted aromatic or heteroaromatic group or can comprise one or more substituted or unsubstituted aromatic or heteroaromatic groups; or a chemical functional group comprising at least one heteroatom; and B has the same meaning as above.

However, repeat units other than those corresponding to the specific formulae (I-A) and (I-B) can also be envisaged, such as, for example, repeat units of general formula (I) in which $A^1$, $A^2$ and $A^3$ are each a thienyl group.

It should be noted that, when $R^5$, $R^6$, $R^7$, $R^8$, $R^9$, $R^{10}$, $R^{11}$, $R^{12}$, $R^{13}$, $R^{14}$, $R^{15}$ and/or $R^{16}$ represent, in the specific formulae (I-A) and (I-B), a hydrocarbon group comprising two carbon atoms or more and when this group comprises one or more heteroatoms and/or one or more chemical functional groups and/or one or more aromatic or heteroaromatic groups, then this(these) heteroatom(s), this(these) chemical functional group(s) and this(these) aromatic or heteroaromatic group(s) can equally well form a bridge inside this hydrocarbon group as to be carried as a side group by it or be situated at its end.

Similarly, when X, $R^1$ and/or $R^2$ represent, in the formulae (a), (b) and (c), a hydrocarbon group comprising two carbon atoms or more and when this group comprises one or more heteroatoms and/or one or more chemical functional groups and/or one or more aromatic or heteroaromatic groups, then this(these) heteroatom(s), this(these) chemical functional group(s) and this(these) aromatic or heteroaromatic group(s) can equally well form a bridge inside this hydrocarbon group, to be carried as a side group by it or be situated at its end.

It should also be noted that, while the hydrocarbon groups capable of being represented by $R^5$, $R^6$, $R^7$, $R^8$, $R^9$, $R^{10}$, $R^{11}$, $R^{12}$, $R^{13}$, $R^{14}$, $R^{15}$ and/or $R^{16}$, in the specific formulae (I-A) and (I-B) and by X, $R^1$ and/or $R^2$ in the formulae (a), (b) and (c) can comprise up to 100 carbon atoms, it is generally preferable for them to comprise not more than 50 carbon atoms and better still no more than 30 carbon atoms. This is also true for all the other $C_1$ to $C_{100}$ hydrocarbon groups envisaged in the context of the present invention. As mentioned above, B can represent, in the general formula (I), a chiral group of C2 symmetry, in which case it can in particular be:

an aliphatic hydrocarbon group, such as, for example, a group corresponding to the formula (i) below:

(i)

in which $R^{17}$ represents a halogen atom; a saturated or unsaturated, linear, branched or cyclic, hydrocarbon group comprising from 1 to 100 carbon atoms, which hydrocarbon group can comprise one or more heteroatoms and/or one or more chemical functional groups comprising at least one heteroatom, and can be a substituted or unsubstituted aromatic or heteroaromatic group or can comprise one or more substituted or unsubstituted aromatic or heteroaromatic groups; or a chemical functional group comprising at least one heteroatom;

a cyclic group comprising a saturated ring, such as, for example, a group corresponding to one of the formulae (ii), (iii) and (iv) below:

in which:

$R^{18}$ and $R^{19}$ represent, independently of one another, a hydrogen or halogen atom; a saturated or unsaturated, linear, branched or cyclic, hydrocarbon group comprising from 1 to 100 carbon atoms, which hydrocarbon group can comprise one or more heteroatoms and/or one or more chemical functional groups comprising at least one heteroatom, and can be a substituted or unsubstituted aromatic or heteroaromatic group or can comprise one or more substituted or unsubstituted aromatic or heteroaromatic groups; or a chemical functional group comprising at least one heteroatom;

W represents an oxygen atom, an NH group or a $CH_2$ group which is optionally substituted by a saturated or unsaturated, linear, branched or cyclic, hydrocarbon group comprising from 1 to 100 carbon atoms, which hydrocarbon group can comprise one or more heteroatoms and/or one or more chemical functional groups comprising at least one heteroatom, and can be a substituted or unsubstituted aromatic or heteroaromatic group or can comprise one or more substituted or unsubstituted aromatic or heteroaromatic groups; or a chemical functional group comprising at least one heteroatom;

an aromatic group, such as, for example, a group derived from 1,1'-binaphthyl corresponding to one of the formulae (v), (vi) and (vii) below:

(v)

-continued in which $R^{20}$, $R^{21}$ and $R^{22}$ represent, independently of one another, a hydrogen or halogen atom; a saturated or unsaturated, linear, branched or cyclic, hydrocarbon group comprising from 1 to 100 carbon atoms, which hydrocarbon group can comprise one or more heteroatoms and/or one or more chemical functional groups comprising at least one heteroatom, and can be a substituted or unsubstituted aromatic or heteroaromatic group or can comprise one or more substituted or unsubstituted aromatic or heteroaromatic groups; or a chemical functional group comprising at least one heteroatom.

However, it is preferable for B to be a group corresponding to one of the formulae (a), (b) and (c) as defined above and in particular for B to be a group of formula (a), (b) or (c) in which X is a chiral hydrocarbon group of C2 symmetry, this being because the combination of the diimine or diamine functionality present in these groups with a chirality of symmetry of C2 type has been shown to result in an optimization at the same time of the chemical affinity of the polymer with regard to nitro compounds, of its fluorescence yield and the porosity of the thin films or of the monoliths prepared from this polymer.

In particular, preference is given to the polymers comprising at least one repeat unit of general formula (I) in which B represents a group corresponding to one of the formulae (a), (b) and (c) where X is a chiral hydrocarbon group of C2 symmetry chosen from the groups corresponding to the formulae (i) to (vii) as defined above.

Preference is very particularly given, among these polymers, to:
  those which comprise at least one repeat unit corresponding to one of the specific formulae (I-A-a), (I-A-b) and (I-A-c) below:

(I-A-a)

(I-A-b)

(I-A-c)

in which $R^5$ to $R^{16}$ are as defined above; and
those which comprise at least one repeat unit corresponding to one of the specific formulae (I-B-a), (I-B-b) and (I-B-c) below:

in which $R^5$, $R^6$, $R^9$, $R^{10}$ and $R^{13}$ to $R^{16}$ are as defined above.

According to yet another preferred arrangement of the invention, in the specific formula (I-A), at least one of $R^5$ to $R^{16}$ represents a linear or branched $C_1$ to $C_{20}$ alkoxy group, that or those of $R^5$ to $R^{16}$ which do not represent an alkoxy group, if there are any, then preferably representing a hydrogen atom.

Similarly, it is preferred, in the specific formula (I-B), that at least one of $R^5$, $R^6$, $R^9$, $R^{10}$ and $R^{13}$ to $R^{16}$ represents a linear or branched $C_1$ to $C_{20}$ and better still $C_5$ to $C_{10}$ alkoxy group, that or those of $R^5$, $R^6$, $R^9$, $R^{10}$ and $R^{13}$ to $R^{16}$ which do not represent an alkoxy group, if there are any, then representing a hydrogen atom.

It is thus possible, by varying the number of alkoxy groups carried by the phenyl and/or thienyl groups and by varying the number of carbon atoms present in these alkoxy groups, to adjust the solubility of the polymer in organic solvents.

According to a particularly preferred arrangement of the invention, the polymer comprises at least one repeat unit of specific formula (I-A-a), (I-A-b) or (I-A-c) in which $R^{14}$ and $R^{15}$ represent a linear or branched $C_1$ to $C_{20}$ and better still $C_5$ to $C_{10}$ alkoxy group, while $R^5$ to $R^{13}$ and $R^{16}$ represent a hydrogen atom.

Such a polymer can in particular be a polymer having, as repeat unit, the unit of specific formula (I-A-a) or (I-A-b) in which $R^{14}$ and $R^{15}$ represent an octoxy group and $R^5$ to $R^{13}$ and $R^{16}$ represent a hydrogen atom.

According to another particularly preferred arrangement of the invention, the polymer comprises at least one repeat unit of specific formula (I-B-a), (I-B-b) or (I-B-c) in which $R^{14}$ and $R^{15}$ represent a linear or branched $C_1$ to $C_{20}$ and better still $C_5$ to $C_{10}$ alkoxy group while $R^5$, $R^6$, $R^9$, $R^{10}$, $R^{13}$ and $R^{16}$ represent a hydrogen atom.

Such a polymer can in particular be a polymer having, as repeat unit, the repeat unit of specific formula (I-B-a) in which $R^{14}$ and $R^{15}$ represent an octoxy group while $R^5$, $R^6$, $R^9$, $R^{10}$, $R^{13}$ and $R^{16}$ represent a hydrogen atom.

In accordance with the invention, the polymer is preferably a homopolymer, that is to say that it is composed of the repetition of a single repeat unit of general formula (I), it being possible for this unit to be repeated up to 10 000 times.

However, in an alternative form, the polymer can also be a copolymer, in which case it can equally well be composed of different repeat units all corresponding to the general formula (I) as comprise one or more repeat units of general formula (I) and one or more repeat units not corresponding to this formula.

Specifically, it may, for example, be of use to include, in the polymer, repeat units resulting from a monomer of the siloxane type, for the purpose of further enhancing its resistance to aging, or from a monomer of the diethynyldibromobenzene or diethynyldiiodobenzene type, in order to confer greater mechanical strength on it.

According to yet another preferred arrangement of the invention, the polymer is present in the sensor in the form of a thin film which covers one or both faces of a substrate.

However, it can also be present in the form of a monolith, such as, for example, a cylinder exhibiting a degree of porosity so as to render accessible, to the compounds to be detected or to be assayed, all the molecules forming the said polymer. When it is provided in the form of a thin film, the latter preferably has a thickness ranging from 10 angstroms to 100 microns.

Such a film can be obtained by any one of the techniques provided to date for producing a thin film on the surface of a substrate, for example:
  by spraying, by spin coating or by drop coating the substrate with a solution comprising the polymer or the composite;
  by dip coating the substrate in a solution comprising the polymer or the composite;
  by the Langmuir-Blodgett technique;
  by electrochemical deposition; or still
  by in situ polymerization, that is to say directly on the surface of the substrate, of a precursor monomer of the polymer.

The substrate and the measurement system of the sensor are chosen according to the physical property of the polymer whose variations, induced by the presence of the compounds to be detected or to be assayed, are intended to be measured by the sensor.

In the case in point, the variations in two physical properties have proved to be particularly advantageous to measure: they are, on the one hand, variations in the intensity of the fluorescence emitted by the polymer and, on the other hand, variations in the weight of this polymer.

Consequently, the sensor is preferably an optical sensor, the operation of which is based on the measurement of the variations in the intensity of the fluorescence emitted by the polymer, or a gravimetric sensor, the operation of which is based on the measurement of the variations in the weight of the polymer.

The operating principle of fluorescence-based optical sensors has been described in particular by B. Valeur in *Molecular Fluorescence: Principles and Applications*, 2002, published by Wiley VCH, New York [3]. Generally, these sensors comprise a substrate made of glass of optical quality, one of the faces of which is covered with a thin film of the sensitive material. The intensity of the fluorescence emitted by the sensitive material can be measured over the whole of the emission spectrum of this material. However, it is preferable to carry out the measurements of fluorescence intensity at the emission wavelength giving the maximum intensity values for the excitation wavelength, resulting, for its part, in the best signal/noise ratio for the acquisition of the fluorescence intensities.

Mention may be made, as examples of gravimetric sensors, of sensors of the quartz microbalance type, SAW (surface acoustic wave) sensors, such as Love wave sensors and Lamb wave sensors, and microlevers.

Preference is more particularly given, among gravimetric sensors, to sensors of the quartz microbalance type. Sensors of this type, the operating principle of which has been described by J. A. O. Sanchez-Pedrono et al. in *Anal. Chem. Acta,* 182, 1986, 285 [4], comprises, schematically, a piezoelectric substrate (or resonator), generally a quartz crystal covered on both its faces with a metal layer, for example a layer of gold or of platinum, acting as electrode. As the sensitive material covers one or both faces of the substrate, any variation in weight of this material is reflected by a variation in the frequency of vibration of the substrate.

Of course, it is also possible to use a polymer as defined above as sensitive material in sensors designed to measure variations in a physical property other than the intensity of fluorescence and the weight, such as, for example, variations in an electrical property, such as the conductivity, or in an optical property other than fluorescence, such as, for example, absorbance.

In accordance with the invention, the sensor can be of multisensor type, that is to say that it can be composed of several individual sensors which comprise sensitive materials different from one another or which are equipped with substrates and measurement systems different from one another, such as, for example, one or more fluorescence-based sensors and/or one or more gravimetric sensors, the essential point being that at least one of these individual sensors comprises a polymer as defined above as sensitive material.

Sensors comprising a polymer as defined above as sensitive material have proved to exhibit numerous advantages, in particular:
- an ability to specifically detect nitro compounds and in particular nitroaromatic compounds with a high sensitivity, since they are capable of detecting their presence at concentrations of less than 1 ppm (part per million) and even at a tenth of a ppm, as well as a specificity with regard to these compounds,
- a speed of response and a reproducibility of this response,
- a stability of the performance over time and, consequently, a very satisfactory lifetime,
- an ability to operate continuously,
- a manufacturing cost compatible with mass production of sensors, a very small amount of polymer (that is to say, in practice, of a few mg) being necessary for the manufacture of a sensor, and
- the possibility of being miniaturized and, consequently, of being readily transportable and handleable on any type of site.

Another subject-matter of the invention is the use of a chemical sensor as defined above in the detection or assaying of one or more nitro compounds, which compounds can exist equally well in the solid, liquid or gas (vapour) form, but are preferably in the gas form.

In accordance with the invention, the nitro compound or compounds intended to be detected or assayed are chosen from nitroaromatic compounds, nitramines, nitrosamines and nitric esters.

Mention may be made, as examples of nitroaromatic compounds, of nitrobenzene, dinitrobenzene, trinitrobenzene, nitrotoluene, dinitrotoluene, trinitrotoluene, dinitrofluorobenzene, dinitrotrifluoromethoxybenzene, aminodinitrotoluene, dinitrotrifluoromethylbenzene, chlorodinitrotrifluoro-methylbenzene, hexanitrostilbene or trinitrophenol (or picric acid).

The nitramines are, for their part, for example, cyclotetramethylenetetranitramine (or octogen), cyclotrimethylenetrinitramine (or hexogen) and trinitrophenylmethylnitramine (or tetryl), while the nitrosamines are, for example, nitrosodimethylamine.

With regard to the nitric esters, they are, for example, pentrite, ethylene glycol dinitrate, diethylene glycol dinitrate, nitroglycerine or nitroguanidine.

According to yet another preferred arrangement of the invention, the sensor is used for the detection or assaying of explosives.

Other characteristics and advantages of the invention will become more clearly apparent on reading the remainder of the description which follows, which relates to examples of sensors according to the invention and of demonstration of their properties, and which refers to the appended drawings.

Of course, these examples are given only by way of illustration of the subject-matter of the invention and do not under any circumstances constitute a limitation on this subject-matter.

DETAILED ACCOUNT OF SPECIFIC EMBODIMENTS

In the examples which follow, 2,4-dinitrorifluoromethoxybenzene (DNTFMB) is used as nitro compound due to its great similarity to dinitrotoluene (DNT), which is the nitro derivative most generally present in the chemical signature of mines based on trinitrotoluene (TNT).

Furthermore, in Examples 1 to 4 and 6, the measurements of intensity of fluorescence are carried out using a Fluoro-Max-3 fluorimeter from Jobin Yvon, under dynamic conditions in a cell swept at 20 l/h. These measurements are carried out using the excitation wavelength of the sensitive material resulting in the best signal/noise ratio for the acquisition of the intensities of fluorescence and at the emission wavelength giving the maximum intensities of fluorescence for this excitation wavelength. The emission and excitation wavelengths thus selected are specified in each example.

Example 1

Detection of DNTFMB by a First Example of a Sensor in Accordance with the Invention In this example, the preparation is carried out of a sensor, the operation of which is based on the variation in the intensity, of the fluorescence emitted by the sensitive material which this sensor comprises in the presence of a nitro compound.

In the case in point, the sensitive material is composed of a polymer comprising a repeat unit of specific formula (I-A-a) in which $R^5$ to $R^{13}$ and $R^{16}$=H and $R^{14}$ and $R^{15}$=$OC_8H_{17}$, in the form of a thin film which covers one of the faces of a substrate made of glass of optical quality.

To do this, the polymer is synthesized from (1R,2R)-diaminocyclohexane and 4-bromobenzaldehyde, as described by J. P. Lere-Porte et al. in the reference [5], and then deposited on the glass substrate by carrying out three sprayings, each of 0.2 second, of a solution of the said polymer in chloroform with a concentration of 1.5 g/l.

The thin film thus obtained exhibits an intensity of fluorescence of $2 \times 10^7$ cps (counts per second; $\lambda_{emission}$: 507 nm; $\lambda_{excitation}$: 404 nm)

The sensor is successively exposed to:
pure nitrogen for 30 minutes,
DNTFMB at a concentration of 0.5 ppm in nitrogen for 10 minutes,
pure nitrogen for 60 minutes,
DNTFMB at a concentration of 0.1 ppm in nitrogen for 10 minutes,
pure nitrogen for 50 minutes,
DNTFMB at a concentration of 0.03 ppm in nitrogen for 10 minutes and, finally,
pure nitrogen for 15 minutes,
the nitrogen and the DNTFMB being, in all cases, in the gas form at ambient temperature.

Figure 1:
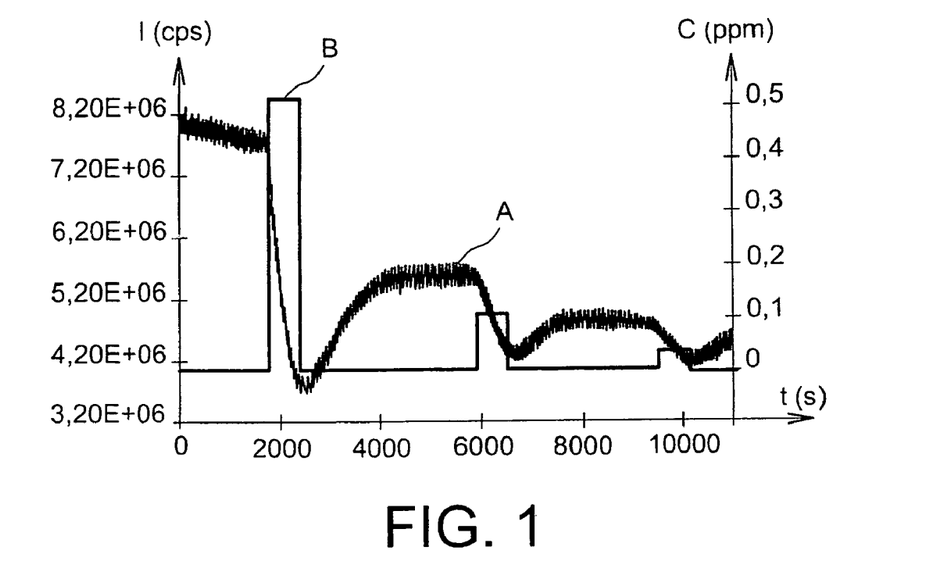
FIG. 1 represents the change in the intensity of the fluorescence emitted by a first example of the sensor in accordance with the invention ($\lambda_{emission}$: 507 nm; $\lambda_{excitation}$: 404 nm) when this sensor is exposed alternately to pure nitrogen and to mixtures of nitrogen and of 2,4-dinitrotrifluoromethoxybenzene (DNTFMB).

FIG. 1 illustrates the change in the intensity of fluorescence emitted by the sensor during these exposures ($\lambda_{emission}$: 507 nm; $\lambda_{excitation}$: 404 nm).

In this figure, curve A represents the values of the intensity of fluorescence (I), expressed in cps, as a function of the time (t), expressed in seconds, while curve B represents the values of the concentration of DNTFMB (C), expressed in ppm, also as a function of the time.

Example 2

Demonstration of the Selectivity of the First Example of a Sensor in Accordance with the Invention for Nitro Compounds with Regard to Solvents In this example, a sensor identical to that described in Example 1 is used.

This sensor is successively exposed to:
pure nitrogen for 90 minutes,
DNTFMB at a concentration of 1 ppm in nitrogen for 10 minutes,
pure nitrogen for 30 minutes,
dichloromethane at a concentration of 675 ppm in nitrogen for 10 minutes,
pure nitrogen for 30 minutes,
cyclohexane at a concentration of 540 ppm in nitrogen for 10 minutes,
pure nitrogen for 30 minutes,
methyl ethyl ketone at a concentration of 360 ppm in nitrogen for 10 minutes,
pure nitrogen for 80 minutes,
toluene in a concentration of 180 ppm in nitrogen for 10 minutes,
pure nitrogen for 25 minutes,
methyl isobutyl ketone at a concentration of 90 ppm in nitrogen for 10 minutes,
pure nitrogen for 30 minutes,
ethyl acetate at a concentration of 720 ppm in nitrogen for 10 minutes,
pure nitrogen for 25 minutes and, finally,
DNTFMB at a concentration of 1 ppm in nitrogen for 6 minutes,
the nitrogen, the DNTFMB and the other solvents being, in all cases, in the gas form and at ambient temperature.

Figure 2:
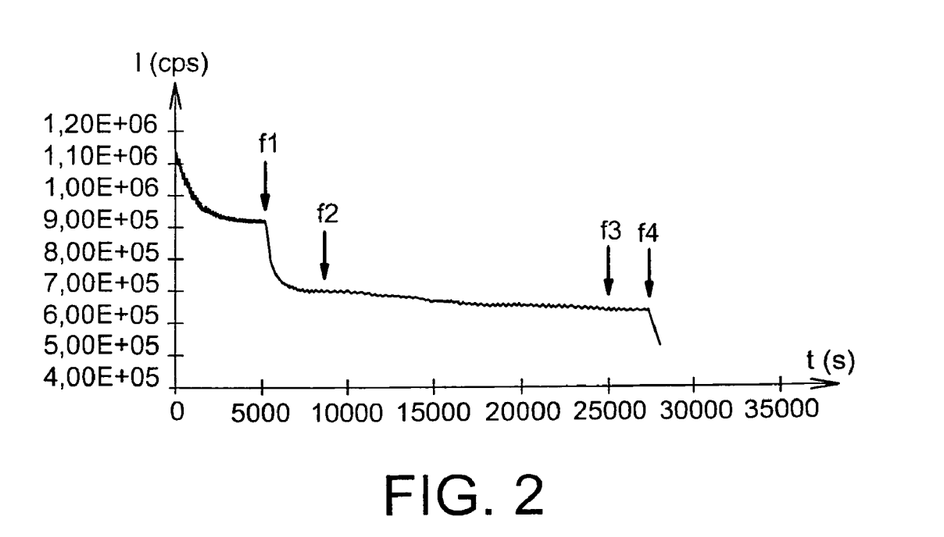
FIG. 2 represents the change in the intensity of the fluorescence emitted by the first example of a sensor in accordance with the invention ($\lambda_{emission}$: 507 nm; $\lambda_{excitation}$: 404 nm) when this sensor is exposed alternately to pure nitrogen and to mixtures of nitrogen and of DNTFMB, dichloromethane, cyclohexane, methyl ethyl ketone, toluene, methyl isobutyl ketone, ethyl acetate and, again DNTFMB, respectively.

FIG. 2 illustrates the change in the intensity of fluorescence (I), expressed in cps ($\lambda_{emission}$: 507 nm; $\lambda_{excitation}$: 404 nm), as emitted by the sensor as a function of time (t), expressed in seconds. The f1 indicates the beginning of the first exposure to the nitrogen/DNTFMB mixture; the f2 indicates the beginning of the exposure to the nitrogen/dichloromethane mixture; the arrow f3 indicates the end of exposure to the nitrogen/ethyl acetate mixture, while the arrow f4 indicates the beginning of the second exposure to the nitrogen/DNTFMB mixture.

This figure shows that the exposure of the sensor to solvents, such as dichloromethane, cyclohexane, methyl ethyl ketone or toluene, does not bring about a response of the sensor comparable to that obtained when the latter is exposed to a nitro compound. Furthermore, the response of the sensor obtained during its second exposure to DNTFMB shows that the solvents have not affected the performance of the sensor with regard to nitro compounds.

Example 3

Demonstration that the Detection Properties of the First Example of a Sensor in Accordance with the Invention are Maintained Over Time In this example, a sensor identical to that described in Example 1 is used.

This sensor is exposed a number of times to DNTFMB at a concentration of 1 ppm in nitrogen, each exposure lasting 10 minutes, the first exposure taking place on the day of the deposition of the thin film of polymer on the glass substrate (D0) and the following exposures at time intervals over a period of 96 days. The sensor is stored in the ambient air between two exposures to DNTFMB.

Figure 3:
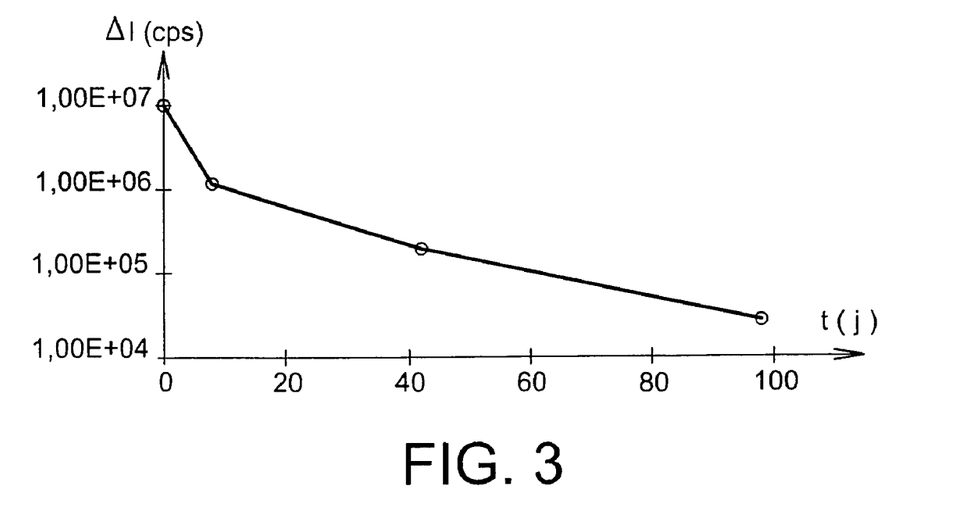
FIG. 3 represents the variation in the intensity of the fluorescence emitted by the first example of a sensor in accordance with the invention ($\lambda_{emission}$: 507 nm; $\lambda_{excitation}$: 404 nm) when this sensor is exposed a number of times to a mixture of nitrogen and of DNTFMB, each exposure lasting 10 minutes and the exposures being spread over a period of 96 days.

FIG. 3 illustrates the values of the variations in the intensity of fluorescence ($\Delta I$) emitted by the sensor during the exposures to the ambient air/DNTFMB mixture carried out D0, D8, D42 and D96 ($\lambda_{emission}$: 507 nm; $\lambda_{excitation}$: 404 nm), these values being determined for each exposure as follows:

$\Delta I$=intensity of fluorescence emitted at the time $t_0$ of an exposure−intensity of fluorescence emitted at the time too min of this same exposure.

This figure shows that, although the variation in the intensity of fluorescence emitted by the sensor tends to fall over time, the sensor is still capable of detecting DNTFMB at the concentration of 1 ppm 96 days after deposition of the thin film of the polymer.

Example 4

Detection of DNTFMB by a Second Example of a Sensor in Accordance with the Invention In this example, the preparation is carried out of a sensor, the operation of which is also based on the variation in the intensity of the fluorescence emitted by the sensitive material of this sensor in the presence of a nitro compound and in which the sensitive material is composed of a polymer comprising a repeat unit of formula (I-A-b) in which $R^5$ to $R^{13}$ and $R^{16}$=H and $R^{14}$ and $R^{15}$=$OC_8H_{17}$, in the form of a thin film which covers one of the faces of a substrate made of glass of optical quality.

The polymer is synthesized from (1R,2R)-diaminocyclohexane and 4-bromobenzaldehyde, as described by J. P. Lere-Porte et al. in the reference [6], and then deposited on the glass substrate by drop coating with a solution of the said polymer in methylene chloride at a concentration of 1 g/l.

The solvent is evaporated at ambient temperature and atmospheric pressure, so as to obtain a thin film exhibiting an intensity of fluorescence of $3.5 \times 10^6$ Cps ($\lambda_{emission}$: 500 nm; $\lambda_{excitation}$: 397 nm)

The sensor is successively exposed to:
pure nitrogen for 45 minutes,
DNTFMB at a concentration of 1 ppm in nitrogen for 10 minutes,
pure nitrogen for 60 minutes,
DNTFMB at a concentration of 0.1 ppm in nitrogen for 10 minutes and, finally,
pure nitrogen for 40 minutes,
the nitrogen and the DNTFMB being, in all cases, in the gas form and at ambient temperature.

Figure 4:
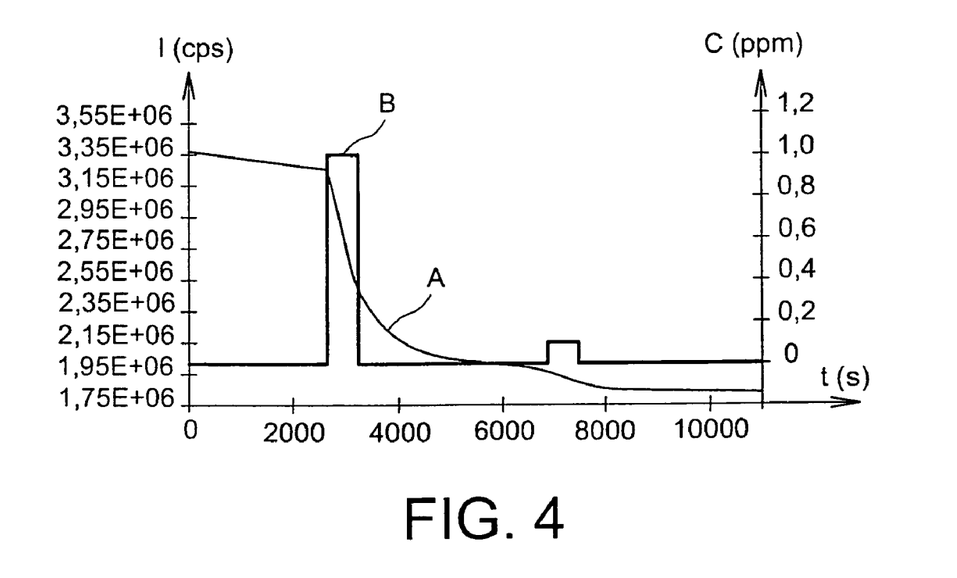
FIG. 4 represents the change in the intensity of the fluorescence emitted by a second example of a sensor in accordance with the invention ($\lambda_{emission}$: 500 nm; $\lambda_{excitation}$: 397 nm) when this sensor is exposed alternately to pure nitrogen and to mixtures of nitrogen and of DNTFMB.

FIG. 4 illustrates the change in the intensity of fluorescence emitted by the sensor during these exposures ($\lambda_{emission}$: 500 nm; $\lambda_{excitation}$: 397 nm).

In this figure, curve A represents the values of the intensity of fluorescence (I), expressed in cps, as a function of the time (t), expressed in seconds, while curve B represents the values of the variation in the concentration of DNTFMB (C), expressed in ppm, also as a function of the time.

Example 5

Detection of DNTFMB by a Third Example of a Sensor in Accordance with the Invention In this example, a quartz microbalance sensor is prepared. To do this, the two faces of an AT-cut quartz crystal with a frequency of vibration of 9 MHz equipped with two circular gold measurement electrodes (QA9RA-50 model, Ametek Precision Instruments) are covered with a thin film of a polymer comprising a repeat unit of specific formula (I-A-a) in which $R^5$ to $R^{13}$ and $R^{16}$=H and $R^{14}$ and $R^{15}$=$OC_8H_{17}$.

This thin film is obtained by carrying out, on each face of the quartz crystal, five sprayings, each of 0.2 second, of a solution of the said polymer in chloroform with a concentration of 1.5 g/l. The formation of this film is reflected by a variation in the frequency of vibration of the quartz of 0.6 kHz.

The sensor is successively exposed to:
ambient air for 9 minutes,
DNTFMB at a concentration of 3 ppm in ambient air for 10 minutes,
ambient air for 38 minutes,
DNTFMB at a concentration of 3 ppm in ambient air for 10 minutes and, finally,
ambient air for 15 minutes.

Figure 5:
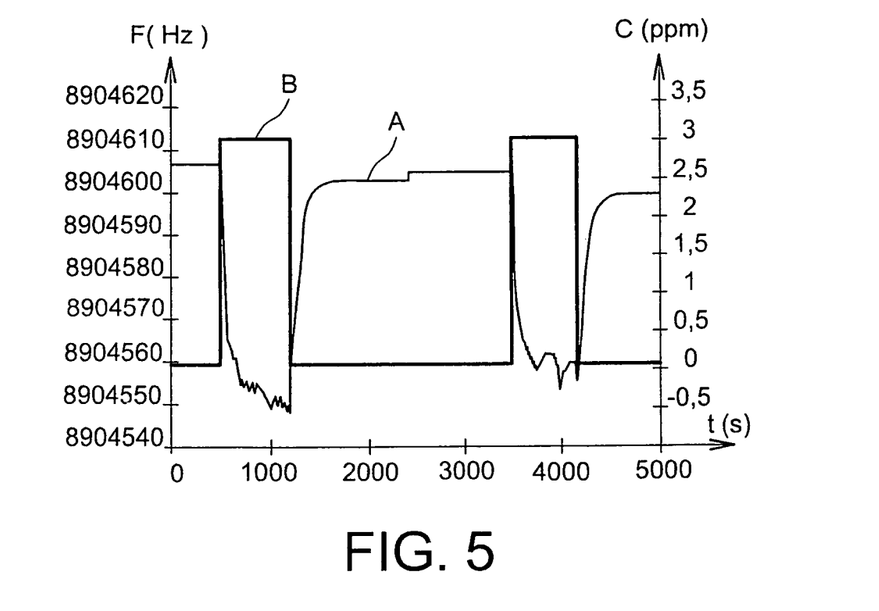
FIG. 5 represents the change in the frequency of vibration of the quartz crystal of a third example of a sensor in accordance with the invention when this sensor is exposed alternately to ambient air and to mixtures of ambient air and of DNTFMB vapours.

FIG. 5 illustrates the change in the frequency of vibration of the quartz crystal during these exposures.

In this figure, curve A represents the values of the frequency of vibration (F), expressed in Hz (hertz), as a function of the time (t), expressed in seconds, while curve B represents the values of the concentration of DNTFMB (C), expressed in ppm, also as a function of the time.

Example 6

Detection of DNTFMB by a Fourth Example of the Sensor in Accordance with the Invention In this example, the preparation is carried out of a sensor, the operation of which is based on the variation in the intensity of this fluorescence emitted by the sensitive material of this sensor in the presence of a nitro compound and in which the sensitive material is composed of a polymer comprising a repeat unit of formula (I-B-a) in which $R^5$, $R^6$, $R^9$, $R^{13}$ and $R^{16}$=H and $R^{14}$ and $R^{15}$=$OC_8H_{17}$, in the form of a thin film which covers one of the faces of a substrate made of glass of optical quality.

The polymer is synthesized from (1R,2R)-diaminocyclohexane and 5-bromothiophene-2-carboxaldehyde, as described by J. P. Lere-Porte et al. in the reference [5], and then deposited on the glass substrate by carrying out 4 sprayings, each of 0.15 second, of a solution of the said polymer in tetrahydrofuran with a concentration of 3 g/l.

The solvent is evaporated at ambient temperature under atmospheric pressure, so as to obtain a thin film exhibiting an intensity of fluorescence of $2 \times 10$ cps ($\lambda_{emission}$: 491 nm; $\lambda_{excitation}$: 397 nm).

The sensor is successively exposed to:
pure nitrogen for 25 minutes,
DNTFMB at a concentration of 400 ppb in nitrogen for 5 minutes and
pure nitrogen for 100 minutes,
the nitrogen and the DNTFMB being in the gas form and at ambient temperature.

Figure 6:
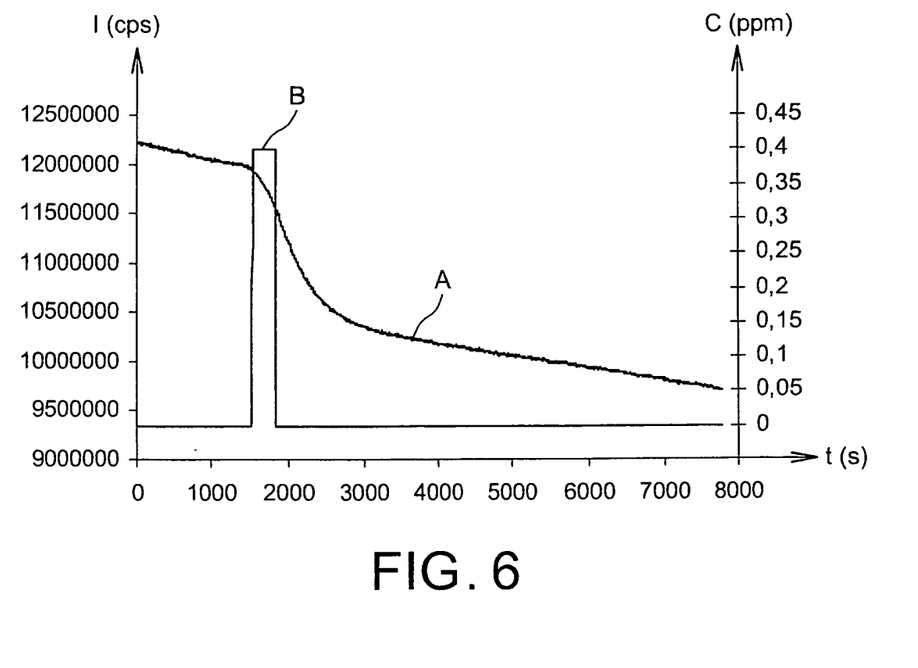
FIG. 6 represents the change in the intensity of the fluorescence emitted by a fourth example of a sensor in accordance with the invention ($\lambda_{emission}$: 491 nm; $\lambda_{excitation}$: 397 nm) when this sensor is exposed alternately to pure nitrogen and to a mixture of nitrogen and of DNTFMB.

FIG. 6 illustrates the change in the intensity of fluorescence emitted by the sensor during these exposures ($\lambda_{emission}$: 491 nm; $\lambda_{excitation}$: 397 nm).

In this figure, curve A represents the values of the intensity of fluorescence (I), expressed as cps, as a function of the time (t), expressed in seconds, while curve B represents the values of the variation in the concentration of DNTFMB (C), expressed in ppm, also as a function of the time.

REFERENCES CITED

[1] M. J. Sailor et al., *SPIE Proceedings*, The International Society of Optical Engineering, 3713, 1999, 54-65

[2] K. J. Albert and D. R. Walt, *Anal. Chem.*, 72, 2000, 1947

[3] B. Valeur, *Molecular Fluorescence: Principles and Applications*, 2002, published by Wiley VCH, New York

[4] J. A. O. Sanchez-Pedrono et al., *Anal. Chem. Acta*, 182, 1986, 285

[5] J. P. Lere-Porte et al., *Chem. Commun.*, 24, 2002, 3020-3021

[6] J. P. Lere-Porte et, al., *Tet. Lett.*, 42, 2001, 3073-3076

The invention claimed is:

1. Method of detecting the presence of at least one nitro compound in a medium, which comprises:
   contacting said medium with a chemical sensor comprising a sensitive material having at least one physical property which is modified on contact with the nitro compound, wherein said sensitive material comprises at least one polymer comprising at least one repeat unit selected from the group consisting of formulas (I-A-a), (I-A-b), (I-A-c), (I-B-a), (I-B-b) and (I-B-c) below:

(I)

(I-A-a)

(I-A-b)

(I-A-c)

(I-B-a)

(I-B-b)

(I-B-c)

in which:

(a)

(c)

$R^5$, $R^6$, $R^7$, $R^8$, $R^9$, $R^{10}$, $R^{11}$, $R^{12}$, $R^{13}$, $R^{14}$, $R^{15}$ and $R^{16}$ represent, independently of one another:
  a hydrogen or halogen atom;
  a saturated or unsaturated, linear, branched or cyclic, hydrocarbon group comprising from 1 to 100 carbon atoms, which hydrocarbon group can comprise one or more heteroatoms and/or one or more chemical functional groups comprising at least one heteroatom, and can be a substituted or unsubstituted aromatic or heteroaromatic group or can comprise one or more substituted or unsubstituted aromatic or heteroaromatic groups; or
  a chemical functional group comprising at least one heteroatom;

said sensor providing a first response when the nitro compound is not present in the medium and providing a second response when the nitro compound is present in the medium, said second response being different from the first response and corresponding to a modification of the physical property of the sensitive material upon exposure to the nitro compound;

measuring a change in the response of the sensor and correlating the change of response to the presence of the nitro compound in the medium.

2. Method according to claim 1, in which the nitro compound is in a gas form.

3. Method according to claim 1, in which the nitro compound is chosen from nitroaromatic compounds, nitramines, nitrosamines and nitric esters.

4. Method according to claim 1, in which the nitro compound is chosen from nitrobenzene, dinitrobenzene, trinitrobenzene, nitrotoluene, dinitrotoluene, trinitrotoluene, dinitrofluorobenzene, dinitrotrifluoromethoxybenzene, aminodinitrotoluene, dinitrotrifluoromethylbenzene, chlorodinitrotrifluoromethylbenzene, hexanitrostilbene, trinitrophenol, cyclotetramethylenetetranitramine, cyclotrimethylenetrinitramine, trinitrophenylmethylnitramine, nitrosodimethylamine, pentrite, ethylene glycol dinitrate, diethylene glycol dinitrate, nitroglycerine or nitroguanidine.

5. Method according to claim 1, in which the nitro compound is a component of explosives.

6. The method of claim 1, in which the polymer comprises at least one repeat unit selected from the group consisting of formulas (I-A-a), (I-A-b), and (I-A-e) in which at least one of $R^5$ to $R^{16}$ represents a linear or branched $C_1$ to $C_{20}$ alkoxy group, that or those of $R^5$ to $R^{16}$ which do not represent an alkoxy group, if there are any, then representing a hydrogen atom.

7. The method of claim 1, in which the polymer comprises at least one repeat unit selected from the group consisting of formulas (I-A-a), (I-A-b) and (I-A-c) in which $R^{14}$ and $R^{15}$ represent a linear or branched $C_1$ to $C_{20}$ alkoxy group while $R^5$ to $R^{13}$ and $R^{16}$ represent a hydrogen atom.

8. The method of claim 7, in which the polymer comprises at least one repeat unit selected from the group consisting of formulas (I-A-a) and (I-A-b) in which $R^{14}$ and $R^{15}$ represent an octoxy group while $R^5$ to $R^{13}$ and $R^{16}$ represent a hydrogen atom.

9. The method of claim 1, in which the polymer comprises at least one repeat unit selected from the group consisting of formulas (I-B-a), (I-B-b), and (I-B-c) in which at least one of $R^5, R^6, R^9, R^{10}$ and $R^{13}$ to $R^{16}$ represents a linear or branched $C_1$ to $C_{20}$ alkoxy group, that or those of $R^5, R^6, R^9, R^{10}$ and $R^{13}$ to $R^{16}$ which do not represent an alkoxy group, if there are any, then representing a hydrogen atom.

10. The method of claim 8, in which the polymer comprises at least one repeat unit selected from the group consisting of formulas formula (I-B-a), (I-B-b) and (I-B-c) in which $R^{14}$ and $R^{15}$ represent a linear or branched $C_1$ to $C_{20}$-alkoxy group while $R^5, R^6, R^9, R^{10}, R^{13}$ and $R^{16}$ represent a hydrogen atom.

11. The method of claim 10, in which the polymer comprises at least one repeat unit of formula (I-B-a) in which $R^{14}$ and $R^{15}$ represent an octoxy group while $R^5, R^6, R^9, R^{10}, R^{13}$ and $R^{16}$ represent a hydrogen atom.

12. The method of claim 1, in which the polymer is a homopolymer.

13. The method of claim 1, in which the sensor comprises a substrate having two faces and the polymer is in the form of a thin film covering one or both faces of the substrate.

14. The method of claim 13, in which the thin film measures from 10 angstroms to 100 microns in thickness.

15. The method of claim 1, in which the sensor is a fluorescence-based optical sensor.

16. The method of claim 1, in which the sensor is a gravimetric sensor.

17. The method of claim 1, in which the sensor is of a multisensor type and in which the sensor comprises one or more fluorescence-based sensors and/or one or more gravimetric sensors, at least one of these sensors comprising at least one polymer comprising at least one repeat unit of general formula (I) as sensitive material.

18. The method of claim 6, in which the polymer comprises at least one repeat unit selected from the group consisting of formulas (I-A-a), (I-A-b) and (I-A-c) in which at least one of $R^5$ to $R^{16}$ represents a linear or branched $C_5$ to $C_{10}$ alkoxy group, that or those of $R^5$ to $R^{16}$ which do not represent an alkoxy group, if there are any, then representing a hydrogen atom.

19. The method of claim 7, in which the polymer comprises at least one repeat unit selected from the group consisting of formulas (I-A-a), (I-A-b) and (I-A-c) in which $R^{14}$ and $R^{15}$ represent a linear or branched $C_5$ to $C_{10}$ alkoxy group while $R^5$ to $R^{13}$ and $R^{16}$ represent a hydrogen atom.

20. The method of claim 9, in which the polymer comprises at least one repeat unit selected from the group consisting of formulas (I-B-a), (I-B-b) and (I-B-c) in which at least one of $R^5, R^6, R^9, R^{10}$ and $R^{13}$ to $R^{16}$ represents a linear or branched $C_5$ to $C_{10}$ alkoxy group, that or those of $R^5, R^6, R^9, R^{10}$ and $R^{13}$ to $R^{16}$ which do not represent an alkoxy group, if there are any, then representing a hydrogen atom.

21. The method of claim 10, in which the polymer comprises at least one repeat unit selected from the group consisting of formulas (I-B-a), (I-B-b) and (I-B-c) in which $R^{14}$ and $R^{15}$ represent a linear or branched $C_5$ to $C_{10}$ alkoxy group while $R^5, R^6, R^9, R^{10}, R^{13}$ and $R^{16}$ represent a hydrogen atom.

* * * * *

UNITED STATES PATENT AND TRADEMARK OFFICE
CERTIFICATE OF CORRECTION

PATENT NO. : 8,178,354 B2
APPLICATION NO. : 11/547598
DATED : May 15, 2012
INVENTOR(S) : Lionel Hairault et al.

It is certified that error appears in the above-identified patent and that said Letters Patent is hereby corrected as shown below:

<u>On the Title Page</u>

In the left column, item (75), after "Joël Moreau, Montpellier" replace "(FX)" with --(FR)--.

<u>In the Claims</u>

In column 19, claim 6, line 11, before "in which at least" replace "(I-A-e)" with --(I-A-c)--.

In column 19, claim 10, line 36, replace "formulas formula (I-B-a)," with --formulas (I-B-a),--.

Signed and Sealed this
Third Day of July, 2012

David J. Kappos
*Director of the United States Patent and Trademark Office*